United States Patent [19]

Nash

[11] Patent Number: 4,686,982

[45] Date of Patent: Aug. 18, 1987

[54] SPIRAL WIRE BEARING FOR ROTATING WIRE DRIVE CATHETER

[76] Inventor: John Nash, 145 Oak St., Downingtown, Pa. 19335

[21] Appl. No.: 746,220

[22] Filed: Jun. 19, 1985

[51] Int. Cl.$^4$ ............................................. A61F 17/32
[52] U.S. Cl. ...................................... 128/305; 464/52
[58] Field of Search ....................... 128/305, 751, 752; 64/2, 2 R; 464/52; 74/501

[56] References Cited

U.S. PATENT DOCUMENTS

| | | |
|---|---|---|
| 1,481,078 | 1/1924 | Albertson . |
| 1,636,038 | 6/1927 | Bolozky et al. . |
| 1,785,345 | 12/1930 | Hasemann . |
| 2,570,335 | 10/1951 | Fitch ............................................. 64/2 |
| 2,761,297 | 9/1956 | Buchsteiner ................................ 64/2 |
| 2,821,092 | 1/1958 | Cordora et al. ......................... 74/501 |
| 3,180,625 | 4/1965 | Wyzenbeek .............................. 259/1 |
| 4,112,708 | 9/1978 | Fukuda .................................. 64/2 R |
| 4,424,045 | 1/1984 | Kulischenko et al. ................. 464/52 |
| 4,445,509 | 5/1984 | Auth .................................... 128/305 |

Primary Examiner—Henry A. Bennet

[57] ABSTRACT

A recanalizing catheter comprising a very small diameter, elongated, flexible tubular member having a distal end at which a tool is mounted for high speed rotation. A flexible drive assembly is located within the tubular member to power the tool. In one embodiment the drive assembly comprises a spiral bearing formed as an elongated cylindrical helix having a central longitudinal passageway extending therethrough, and a flexible drive shaft extending through the passageway and freely rotatable therein. The tool is mounted at the end of the flexible drive shaft. In another embodiment the drive assembly comprises a spiral drive shaft formed of at least one elongated cylindrical helix having a central longitudinal passageway extending therethrough, and an elongated flexible bearing shaft extending through the passageway and about which the spiral shaft can be freely rotated. The tool is mounted at the end of the spiral shaft. In either embodiment the drive shaft and the bearing cooperate with each other to keep the drive shaft centered even as the device is bent through a sharp radia of curvature, while also preventing the shaft from going into critical whirl as it is rotated at a high rate of speed from a remotely located motor.

32 Claims, 10 Drawing Figures

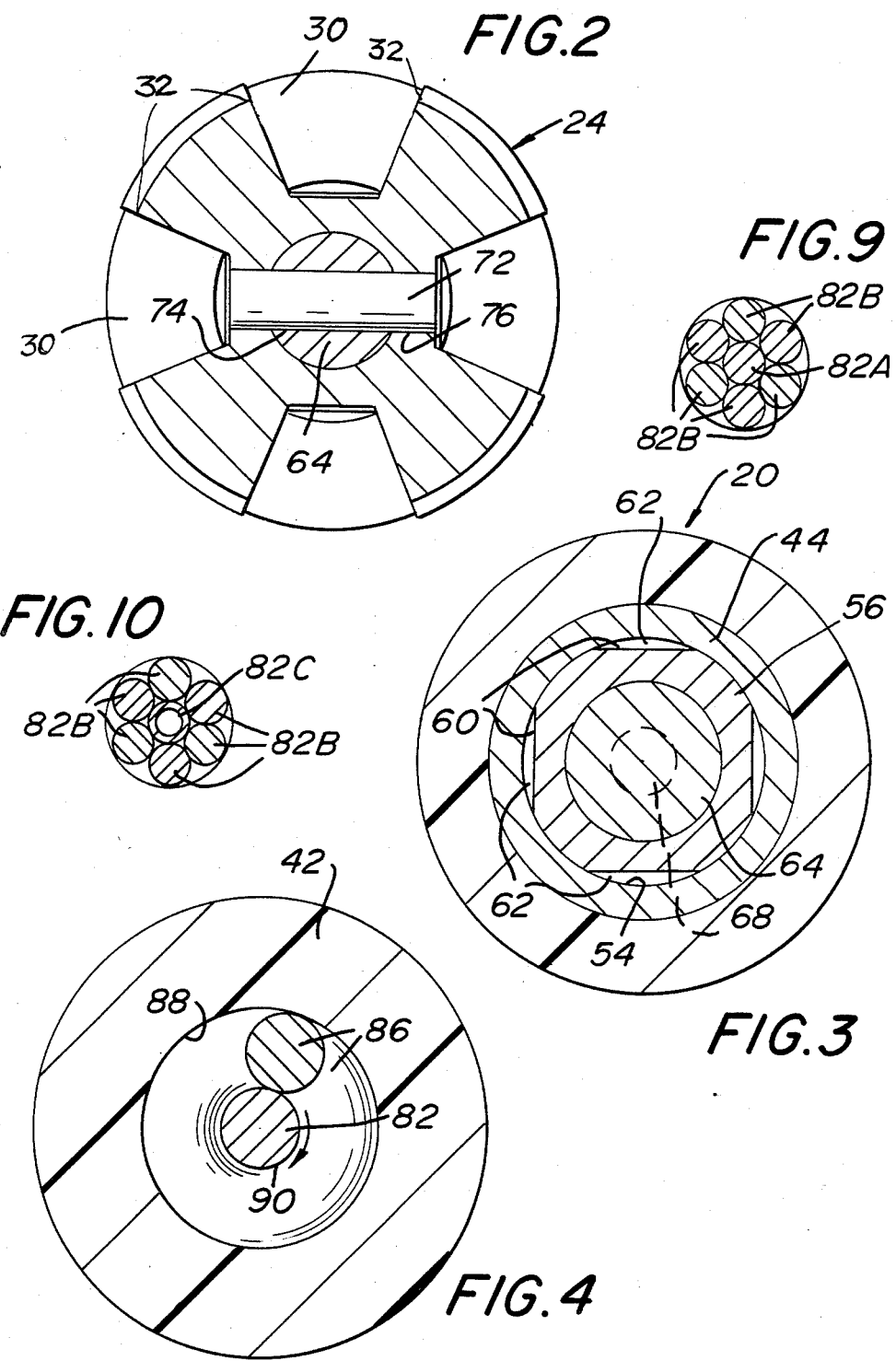

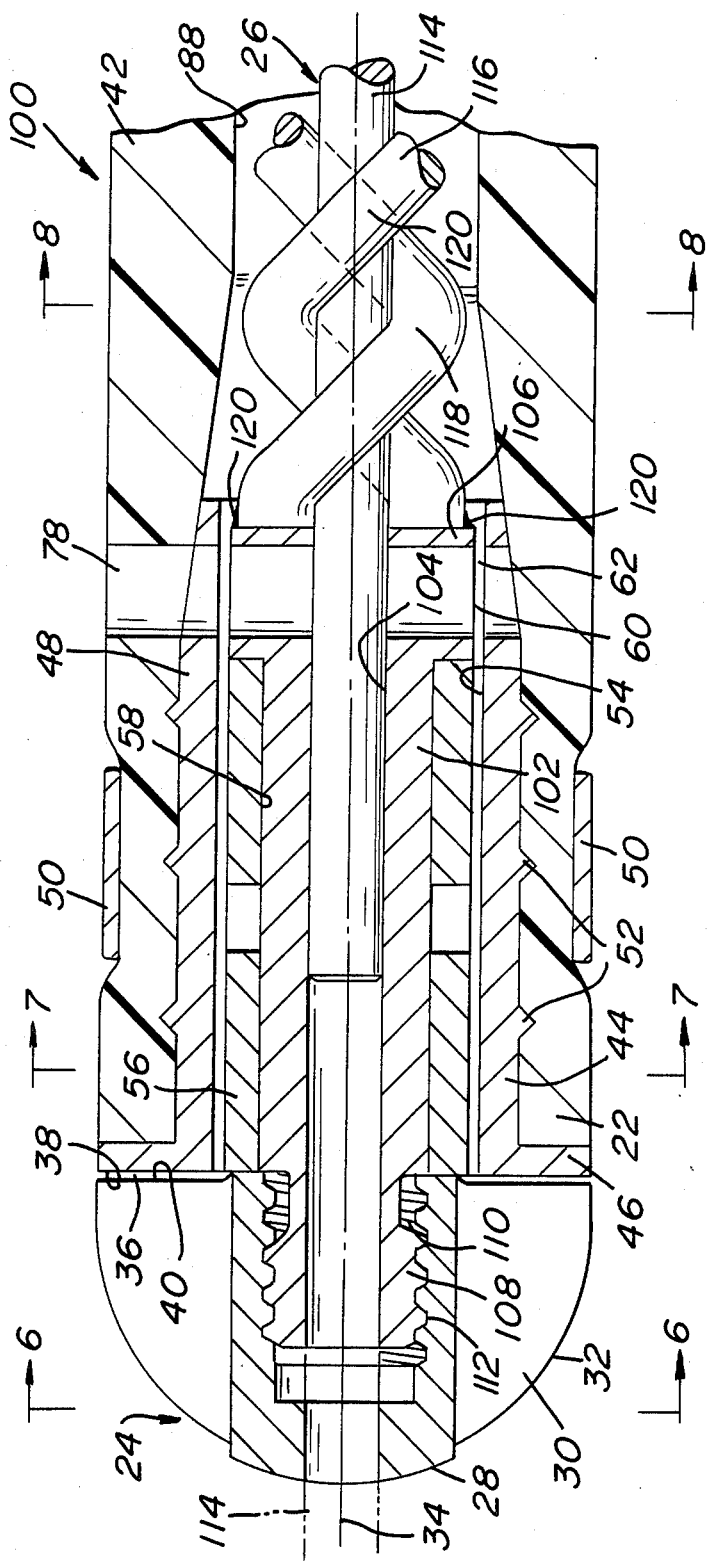

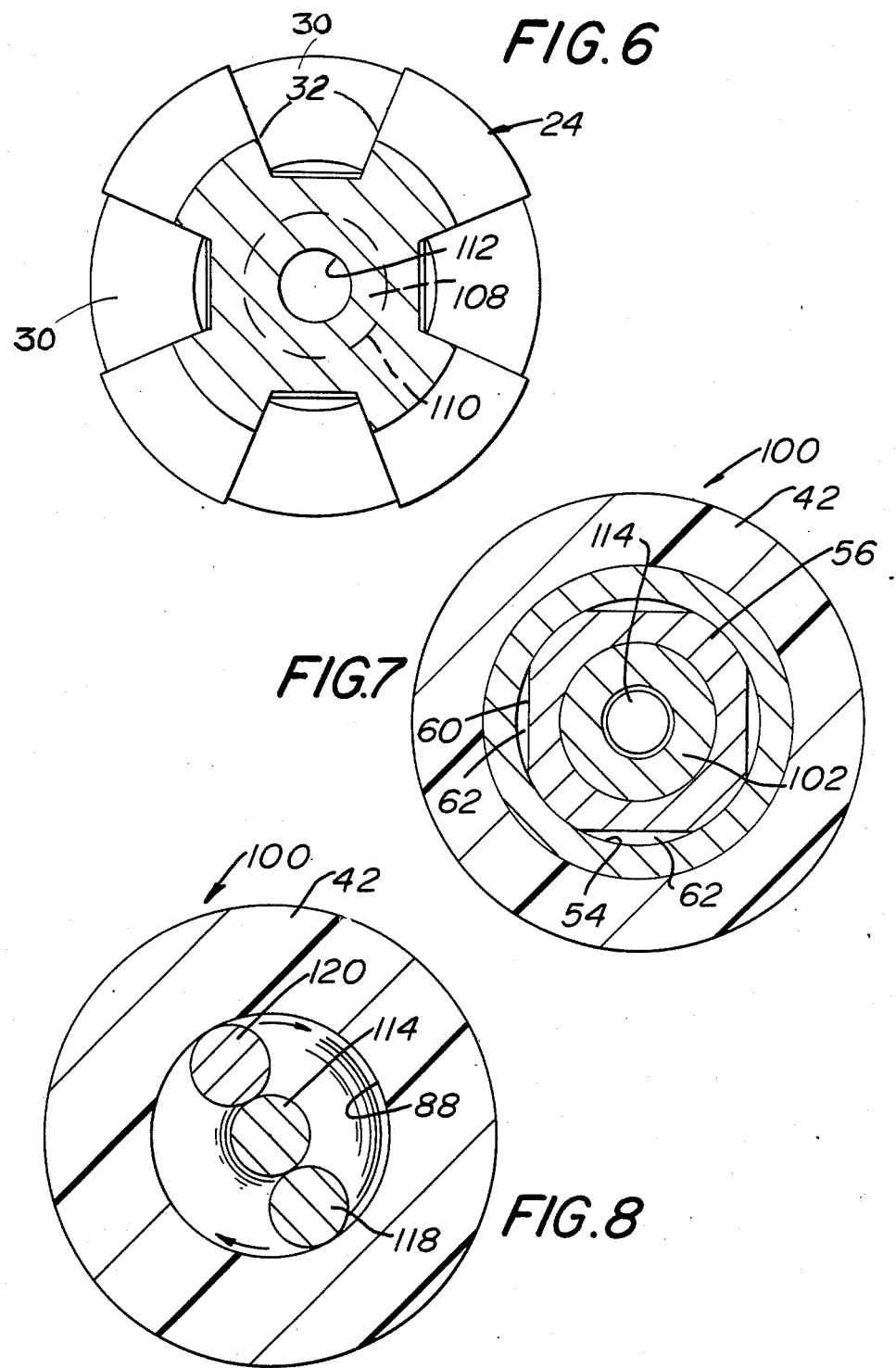

SPIRAL WIRE BEARING FOR ROTATING WIRE DRIVE CATHETER

BACKGROUND OF THE INVENTION

This invention relates generally to flexible drive devices and more particularly to flexible drive, recanalizing catheters for intravascular surgery.

In U.S. Pat. No. 4,445,509 (Auth) there is disclosed a catheter apparatus for recanalizing (opening) a passageway, e.g., and artery, which has been occluded by intra-arterial deposits of atherosclerotic plaque. That recanalization catheter includes a multi-fluted, rotary cutting head mounted at the distal end of the catheter and arranged to be rotated by a flexible drive shaft extending down the center of the catheter. The drive shaft is arranged to be rotated within the catheter by an electric motor coupled to the proximal end thereof. The drive shaft is disclosed as being a steel helical coil of approximately 0.05 inch (1.3 mm) diameter. Such a coil is stated in the patent to be successful in transmitting high rotational speed (greater than 25,000 rpm) in a controlled fashion and with mechanical security.

In order for a recanalizing catheter to have wide applicability of use in intravascular surgery, its length should be sufficiently large, e.g., 2 to 3 feet or more, while its outside diameter, at least adjacent the working end, is sufficiently small, e.g., 3-4 mm. Moreover the catheter should be able to bend through a minimum diameter radius of curvature of 3 inches or less, in order to reach small, remotely located restrictions, e.g., occlusions.

As will be appreciated by those skilled in the art the torsional shear stress produced on a flexible drive shaft (e.g., a wire) will differ for different composition wires, e.g., approximately 150,000 psi for steel wires, 70,000 psi for beryllium-copper wires. If the radius of curvature through which the drive shaft must bend is very small, e.g., less than 3 inches, high bending stresses will be induced therein. In order to reduce bending strain the diameter of the flexible drive shaft or wire must be made very small, e.g., 0.02 or less inches. If the restriction opening tool is to be operated at a high rate of speed, e.g., greater than 20,000 rpm, in order to provide sufficient power at low torque, the deleterious dynamic effects of critical whirl and friction caused by high side loads on the bearing surfaces supporting the drive wire must be overcome or minimized while the positional neutrality (centering) of the drive shaft is maintained in order to insure that proper operation ensues. The flexible drive systems of the prior art as set forth above appear to leave much to be desired from the standpoint of effectiveness and efficiency of operation in applications involving high speed, small diameter, and small radius of curvature.

In my copending U.S. patent application Ser. No. 06/701,063, filed on Feb. 13, 1985, entitled Shaft Driven, Flexible Intravascular Recanalization Catheter, which application is assigned to the same assignee as this invention, and whose disclosure is incorporated by reference herein there is disclosed and claimed a flexible drive assembly for use with recanalization catheters which overcomes the above noted disadvantages of the prior art. To that end the drive assembly as set forth in that application is a flexible assembly which is arranged to be disposed within a very small diameter, elongated, flexible tubular member having a distal end at which a tool, e.g., a cutter, is mounted for high speed rotation.

The drive assembly includes a flexible drive shaft, e.g., a continuous length solid bodied or tubular wire or group of wires, which is mounted within plural spaced bearings to enable it to be rotated at a very high rate of speed from a remotely located motor. The bearings each basically comprise ball-like members having a central opening through which the drive shaft extends. The ball-like bearing members are spaced apart by plural spacer elements at a distance no greater than one-half the wave length of the standing wave which would naturally result from the rotation of a correspondingly sized but unsupported wire at the rotational speed. Each spacer element basically comprises an elongated tubular member having a pair of flared ends. Each of the ball-like bearing members is located between the trailing flared end of one spacer member and the leading free end of the next succeeding, proximally located spacer. Thus, the bearings and associated spacers serve to keep the drive shaft centered even as the catheter is bent through a sharp radius of curvature, while also preventing the shaft from going into critical whirl. A cooling fluid is preferably provided throughout the interior of the tubular member to cool and lubricate the bearings and driveshaft.

While the invention disclosed and claimed in my above noted copending application is suitable for its intended purposes, it is nevertheless somewhat complex in construction. Hence the need exists for a flexible drive shaft having a simple and inexpensive bearing system for supporting an elongated rotary drive element at a central or neutral position while precluding it from going into critical whirl.

Various U.S. patents relate to powered drive shafts, particularly flexible drive shafts and including spirally wound bearings. For example, U.S. Pat. No. 3,180,625 (Wyzenbeek) discloses a flexible shaft having an outer casing enclosing a rotating core and providing a mouth for a spirally wound bearing. The bearing includes a rib for supporting the rotating core. U.S. Pat. No. 4,112,708 (Fukuda) discloses a flexible drive cable having a rotary flexible core member formed of plural strands. The core is supported in a tubular elongated liner member. In some embodiments the liner member is in the form of spirally disposed surfaces to provide plural lubrication grooves therebetween. U.S. Pat. No. 1,785,345 (Hasemann) discloses an elongated flexible shaft such as used with an automobile speedometer located within a casing forming a bearing for the shaft. The cable is supported by a strip formed in a spiral and made of a wear-resisting hard metal. U.S. Pat. No. 2,821,092 (Cordoro et al.) discloses a rotary drive cable to which is fixedly secured a spiral element. The element serves to hold and position the central core within a liner and is formed of Teflon.

While the devices in all of the foregoing patents may be suitable for their intended purposes, none appears suitable for high speed operation in very confined, small radius of curvature applications, where drive element positional neutrality and resistance to critical whirl is of major importance, such as exists in an intravascular catheter device.

Other prior art devices utilizing flexible drive shafts for conveying rotary power to a working head or tool are disclosed in the following U.S. Pat. Nos.: 1,481,078 (Albertson), 1,636,038 (Bolozsky et al.), 2,570,335 (Fitch), 2,761,297 (Buchsteiner et al) and 4,424,045 (Kulischenko et al).

OBJECTS OF THE INVENTION

Accordingly, it is the general object of the instant invention to provide a flexible drive assembly which overcomes the disadvantages of the prior art.

It is a further object of the instant invention to provide a flexible drive assembly which is simple in construction and low in cost.

It is still a further object of the instant invention to provide a flexible drive assembly for use in a intravascular recanalizing catheter or other elongated flexible drive shaft medical instrument and which is simple in construction and low in cost.

It is still a further object of the instant invention to provide a flexible drive assembly for use in a recanalizing catheter and which is simple in construction, of very small diameter, can be bent through a small radius of curvature, while operating at a high rate of speed and, without the drive assembly going into critical whirl.

It is still a further object of this invention to provide a flexible drive assembly for use in a recanalizing catheter which is simple in construction, a very small diameter, can be bent through a small radius of curvature yet which maintains positional neutrality with respect to the catheter at all times.

SUMMARY OF THE INVENTION

These and other objects of the instant invention are achieved by providing a catheter for introduction into a lumen in a living being. The catheter is an elongated flexible member having a distal end at which a working head is located. The working head is arranged to be rotated by a drive assembly. The drive assembly includes elongated drive means for the working head and which extends through the catheter from the working head to a first remote, proximal location. The drive assembly also includes elongated bearing means which extends within the catheter from a point adjacent the working head to a second remote, proximal location. One of the drive means or the bearing means is formed as a spiral of at least one wire wrapped about the other of said means, whereupon the drive means can be rotated freely with respect to the other means and to the catheter to effect the rotation of the working head. The drive means and the bearing means cooperate with each other to maintain the drive means at a neutral position within the catheter as the catheter is bent through any arc up to a minimum radius of curvature, while enabling the drive means to be rotated at a high rotational speed without going into critical whirl.

DESCRIPTION OF THE DRAWING

Other objects and many of the attendant advantages of the instant invention will become readily appreciated when the same becomes better understood by reference to the following detailed description when considered in connection with the accompanying drawing wherein:

FIG. 2 is a sectional view taken along line 2—2 of FIG. 1;

FIG. 3 is a sectional view taken along line 3—3 of FIG. 1;

FIG. 4 is a sectional view taken along line 4—4 of FIG. 1;

FIG. 5 is a side elevational view, partially in section, showing the distal end of an alternative catheter device in accordance with this invention;

FIG. 6 is a sectional view taken along line 6—6 of FIG. 5;

FIG. 7 is a sectional view taken along line 7—7 of FIG. 5;

FIG. 8 is a sectional view taken along line 8—8 of FIG. 5.

FIG. 9 is an enlarged sectional view of an alternative embodiment of a drive wire or guide wire for a catheter constructed in accordance with this invention; and FIG. 10 is an enlarged sectional view of yet another alternative embodiment of a drive wire or guide wire for a catheter constructed in accordance with this invention.

DETAILED DESCRIPTION OF PREFERRED EMBODIMENT

Figure 1:
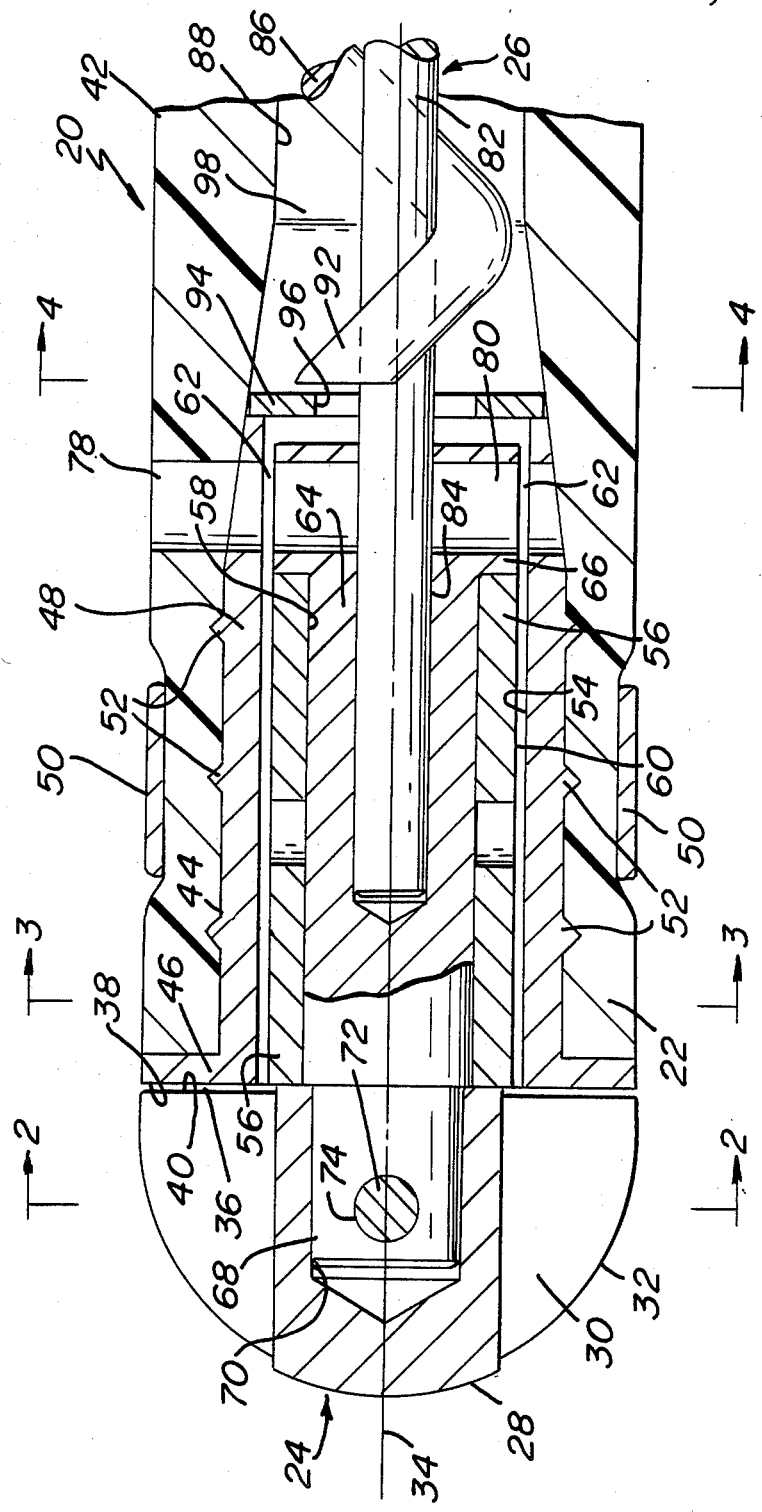
FIG. 1 is a side elevational view, partially in section, showing the distal end of a catheter constructed in accordance wtih this invention.

Referring now in greater detail to the various figures of the drawing wherein like reference characters refer to like parts, there is shown at 20 in FIG. 1 the distal end of a recanalizing catheter 20 for intravascular or other surgical applications. The catheter 20 includes a flexible drive assembly constructed in accordance with this invention. That drive assembly will be described in considerable detail later and is particular suited for intravascular surgical applications, but can be use for other applications requiring the transmission of power at high speed and low torque through a very narrow path including bends of small (minimum) radius of curvature, e.g., 3 inches (7.62 cm). The catheter 20 is an elongated, flexible device, having a distal end portion 22 at which a working head or tool 24 is mounted, and a proximal end portion (not shown) which is adapted to be connected to a source of rotary power, e.g., an electric motor (not shown). The catheter 20 includes the heretofore mentioned drive assembly, now designated by the reference numeral 26, and which extends the length of the catheter to drive, e.g., rotate, the working head under the power provided from the remote power source (motor).

In use, catheter 20 is introduced into the vascular system of the patient such as through an opening in the femoral artery at the point in the groin of the patient remote from the site of the vascular occlusion or blockage that has been determined to exist in an artery, e.g., a coronary artery. The catheter is then passed via the aorta into the heart and then into the desired coronary artery to the point at which the working head is located immediately adjacent the restriction, e.g., partial occlusion or full occlusion. As will be recognized by those skilled in the art such restrictions are formed by the deposit of atherosclerotic plaque or some other material(s), such as waxy and/or calcified atheroma; thickened and/or ulcerated intima, etc.

In the catheter embodiment shown herein the working head or tool 24 comprises a rotary cutter. The cutter is mounted at the distal end of the drive assembly. The cutter basically comprises a solid bodied element of whose outer surface 28 is of generally convex shape and which is provided with four recesses 30 therein. The intersection of each of the walls of each recess 30, with the convex surface of the cutter, forms an arcuate cutting edge or blade 32. In accordance with the preferred embodiment of the invention each arcuate blade 32 includes at least one surface portion having zero or negative rake, with the rake being preferrably negative at an angle of approximately 10° to 30°.

The cutter head 24 is arranged to be rotated at a high rate of speed, e.g., in excess of 20,000 rpm, about the longitudinal central axis 34 of the catheter under power provided from the remote power source, via the flexible drive assembly 26. In order to cool and lubricate the drive assembly a fluid, e.g., water or an oxygenated liquid, is passed through the interior of the catheter from an entrance point adjacent the proximal end thereof. Moreover, the fluid is arranged to exit from the catheter at the distal end 22 thereof through a narrow interface 36 formed between the distal end surface 38 of the catheter itself land the proximal face of the cutter head 24. The exiting fluid has the advantageous effect of providing positive pressure to the wall of the artery contiguous with the cutter 24. In addition the flow of fluid outward through the interface 36 also precludes fine fiberous tissue of the artery from gaining ingress into the interface where it could snag or spool-up. Moreover, the rotating cutter blades impart momentum to the exiting fluid, which action applies further positive pressure to the artery wall, thereby further decreasing the chances of tissue-snagging.

The restriction opening process is carried out by advancing the catheter 20 as the cutter head 24 rotates into the material making up the restriction so that the rotating cutter blades engage that material. In some instances, e.g., hard or calcified deposits, an opening in the restriction is created by the rotating cutter blades actually cutting away or emulsifing particles of the material(s) making up the restriction. In other instances, e.g., waxy or soft deposits, the material(s) of the restriction may merely be mechanically agitated, beaten, stretched or otherwise disturbed by the blades of the rotating cutter, whereupon an opening is created in the restriction by the movement of the material(s) without such material(s) actually being cut-up or removed from the restriction. In either case, an opening permitting the freer flow of blood through the restriction results.

The details of the catheter 20 will now be described. As can be seen the catheter 20 basically comprises an elongated, flexible tubular member 42 which is formed of a sutiable material, e.g., plastic, and which has a small outside diameter. In the preferred embodiment shown herein the outside diameter is approximately 3 mm (10 French) or less, while the inside dimeter of the catheter tube is approximatly 1.5 mm (5 French). At the distal end 22 of the catheter tube 42 there is secured a sleeve-like outer bushing 44. The outer bushing forms one portion of the mount for the cutter 26. The bushing 44 is in the form of a distal flanged portion 46 and an elongated tubular body portion 48. The flanged portion 46 forms the distal end of the catheter and in particular the distal surface portion 38 described heretofore. The elongated tubular portion 48 of the bushing extends within the distal end of the catheter tube 42 and is held in place by the use of a retaining band 50. Thus, the retaining band 50 tightly encircles the periphery of the catheter tube 42 to cause plural gripping teeth 52 in the periphery of the bushing portion to dig into the interior surface of the catheter tube and thereby hold the bushing tightly in place therein. Disposed within the central passageway 54 of the outer bushing 44 is an inner bushing 56. The inner bushing 56 is fixedly mounted within the outer bushing 44 and is also formed of a tough, wear resistant, yet low friction material, such as beryllium-copper.

As can be seen in FIGS. 1 and 3 the inner bushing 56 is an elongated member having a central circular passageway 58 extending therethrough. The outer periphery of the inner bushing 56 is of generally circular profile but includes four, equadistantly spaced flatted surface portions 60 (FIG. 3). Each surface portion extends the full length of the inner bushing 56 so as to define a space 62 between it and the cylindrical interior surface of the outer bushing 44. Each of the spaces 62 is in communication with the open interface 36 between the cutting head and the distal end of the catheter to serve as passageway for carrying liquid from the interior of the catheter out through the interface 36 for the reasons described heretofore. As will be described later this liquid also serves to cool and lubricate the moveable members of the flexible drive assembly 26 to facilitate operation of the catheter.

A cutter-mounting shaft 64 is located within the central bore 58 in the inner bushing 56 and extends along its central axis 34 and is arranged to freely rotate within the inner bushing about axis 34. As can be seen the shaft 64 includes a flanged proximal end 66 and a reduced diameter distal end 68. The distal end 68 extends beyond the distal end 38 of the catheter for disposition and securement within a mating central bore 70 in the cutter tip 24. The cutter tip is fixedly secured to the distal end of the mounting shaft 64 via a retainer pin 72 extending through aligned holes 74 and 76 in the cutter tip mounting shaft 64 and cutter tip 24, respectively, (FIG. 2).

A spragging port 78 extends through the catheter tube sidewall 42. An associated spragging port 80 is provided in the flanged portion 66 of the cutter tip mounting shaft 64. The spragging port 80 extends diametrically with respect to the flange 66 so that it can be aligned with spragging port 78 to lock the rotary position of the tip 24 with respect to the catheter, when such action is desired, e.g., during maintenance and adjustment of the device.

The flexible drive assembly 26 basically comprises an elongated drive wire or shaft 82 which extends the length of the catheter from the remote, proximally located power source to the cutter tip mounting shaft 64. The drive shaft 82 is secured to the cutter tip mounting shaft 64. In particular the distal end of the drive shaft 82 extends into a central bore 84 therein and is fixedly secured in place in the bore 84 by any suitable securement means.

The drive shaft 82 is arranged to be rotated about its longitudinal axis 34 at a high rate of speed to cause the concomitant rotation of the cutter tip 24. In order to support the drive shaft 82 at a central (neutral) position within the catheter tube along its length, irrespective of bends in the catheter up to a minimum radius of curvature, e.g., 3 inches, while also preventing the drive shaft from going into critical whirl, the flexible drive assembly 26 also includes an elongated bearing member 86. As can be seen, the bearing member 86 comprises a helical or spiral cylindrical coil of wire surrounding the flexible drive shaft 82. The spiral bearing extends substantially the entire length of the catheter from a proximately located point adjacent the motor (not shown) to the distal end 22 of the catheter.

As can be seen in FIG. 4 the outer diameter of the helical coil bearing 86 is sufficiently great so that its loops just clear the interior surface 88 of the catheter tube 44 to hold the bearing 86 securely centered in place therein. The inside diameter of the central passageway 90 extending down the length of the coil bearing 86 is just slightly greater than the outside diameter of the flexible drive shaft 82 so that the drive shaft 82 can rotate freely therein as shown by the arrows in FIG. 3.

As shown in FIG. 1 the distal end 92 of the coil bearing 86 is connected to a stationary disk-like wall retaining member 94 which is fixedly secured to the proximal end of the outer bushing 44. The wall 94 includes a central opening 96 therein and through which the flexible drive shaft 82 extends. The diameter of the opening 96 is sufficiently large to enable liquid which is introduced into the tubular space 98 within the catheter at the proximal end thereof to flow from that space through opening 96 and into the longitudinally extending passages 62 for egress from the interface 36. The securement of distal end 92 of the helical coil bearing 86 to the stationary wall 94 is effected by any suitable means, such as welding.

As will be appreciated by those skilled in the art inasmuch as the helical bearing surrounds the drive shaft 82 along its full length while keeping the drive shaft centered, the drive shaft is in effect held in position along its entire length and cannot thus go into critical whirl.

In order to insure that the catheter is sufficiently flexible to negotiate short radia of curvature, while not presenting an undue impediment to the flow of cooling fluid through the passageway 98 in the catheter, the diameter of the wire making up the helical coil and the pitch of the coils loop and the pitch of the helical coil bearing 86 are appropriately selected. In the embodiment shown and described herein the diameter of the wire making up the helical coil is approximately 0.01 inch (0.25 mm) and the helix angle of each coil is approximately 45°. This construction optimizes bending, flexibility, torsional strength and fluid flow passage. It must be pointed out that the wire diameter and/or helix angle of the helical bearing may be other dimensions, if desired, and depending upon the application. As will be appreciated of course, the shorter the helix angle the more convolutions of the helix and hence the greater distance through which fluid must flow.

In accordance with the preferred embodiment of the invention the helical coil bearing 86 is formed of a strong, yet flexible, low friction material, such as heat treated beryllium-copper.

It must be pointed out at this juncture that the drive shaft or wire 82 may be formed from multiple elements in lieu of the single wire or tube described heretofore. Thus, as shown in FIG. 9 the drive shaft can be a rope consisting of a central wire 82A surrounded by six helical wires 82B. Alternatively the central wire can be a tube 82C as shown in FIG. 10 surrounded by six helical wires 82B.

Referring now to FIG. 5 there is shown an alternative embodiment of the recanalizing catheter constructed in accordance with the subject invention. The embodiment shown in FIG. 5 is denoted by the reference numeral 100 and is identical in many respects to the embodiment 20 disclosed heretofore. To that end all common features are given the same reference numerals as given with respect to embodiment 20. The major difference in the embodiment in FIG. 5 is that the catheter includes a central passageway extending down its length through which a conventional guide wire can pass to facilitate the placement of the catheter at the desired intravascular position. In order to make use of that central passageway the flexible drive assembly of the embodiment of FIG. 5 includes an elongated drive shaft, which as will be described in considerable detail later comprises a double helical coil having a longitudinally extending passageway therethrough and through which the guide wire can pass. Also, as can be seen in FIG. 5 the cutter tip of embodiment 100 is thread-mounted, as opposed to being pin mounted like that of the embodiment of FIG. 1.

Inasmuch as many of the features of the catheter 100 of FIG. 8 are the same as that described heretofore and using the same reference numerals, such parts will not be described in detail in the description of FIG. 5 to follow.

Disposed within the central passageway 58 of the inner bushing 56 is a cutter tip mounting shaft 102. The shaft 102 is an elongated cylindrical member having a central passageway 104 extending longitudinally therethrough. The distal end of the shaft 102 is denoted by the reference number 108 and extends beyond the front face 38 of the outer bushing. The projecting portion 108 includes helical threads 110 extending about the periphery thereof. A matingly threaded bore 112 extends into the cutter tip 24 and is arranged for threaded receipt of the projecting portion 108 of shaft 102 to mount the tip on the shaft. A central passageway 112 is also provided in the cutter tip 24 and is aligned with the passageway 104 on the tip mounting shaft 102. It is through the aligned passages 112 and 104 at the distal end of the catheter that the member (e.g., guide wire) forming the bearing surface for the drive shaft of the flexible drive assembly 26 passes. That guide wire used in the catheter 100 is denoted by the reference numeral 114, and can be of any conventional construction used to guide a catheter to an appropriate intravscular position.

As can be seen clearly in FIGS. 5 and 8 the flexible drive shaft 116 itself comprises a pair of cylindrical helical (spiral) wires which are interlaced with each other and which extend about the guide wire 114 for substantially the entire length of the catheter tube 42. The two helical wiers forming the elongated drive shaft 116 are specifically denoted by the reference numerals 118 and 120, and each is fixedly secured at its distal end to the flanged end 106 of the cutter tip mounting shaft 102 by suitable means, e.g., weld joints 120.

As can be seen clearly in FIG. 8 the outside diameter of the interlaced coils making up the flexible drive shaft 116 are each slightly less than the inside diameter 88 of the catheter tube 42 to enable the drive shaft 116 to freely rotate about its central axis 34. Moreover, the two helical wires 118 and 120, when interleaved define a longitudinally extending central passageway 122 therethrough. The outside diameter of the passageway 122 is just slightly greater than the outside diameter of guide wire 114 to enable the two spiral wires 118 and 120 making up the drive shaft 116 to rotate as a unit about the guide wire. The proximal end of the flexible drive shaft 116 is connected by means (not shown) to the electric motor (not shown) to effect such rotation, and hence power the catheter 100.

As will be appreciated by those skilled in the art with the guide wire 114 in place it is centered in the catheter tube 42 by the passageway 104 at the distal end thereof and by appropriate centering means (not shown) at the proximal end thereof. Since the outer periphery of the coils making up the helical drive shaft 116 are spaced slightly from the inner surface of the catheter tube the shaft is enabled to rotate freely about the guide wire, while being centered within the catheter tube notwithstanding the fact that the tube 42 may bend around relatively sharp radia of curvature, e.g., 3" (76 mm). Moreover, inasmuch as the helical drive wires 118 and 120 are supported by the guide wire 114 passing therethrough along substantially the entire length thereof the drive shaft 116 formed by those wires is precluded from going into critical whirl, irrespective of the speed of rotation.

The rotation of the helical drive shaft 116 creates a pumping effect so that the cooling (lubricating) liquid introduced into the interior of the tubular catheter 42 at a proximal location is pumped down the length thereof. Accordingly, that liquid flows to the distal end of the catheter and through communicating passageway 62 and interface 36 out of the catheter contiguous with the tip 24. This action, is noted heretofore, has the effect of preventing snagging of the cutting tip while also insuring damage to the patients vascular system does not arise.

In accordance with the embodiment of the invention shown in FIG. 5 each of the wires 118 and 120 forming the flexible drive shaft 116 is of 0.01 inches (0.25 mm) outside diameter, with the pitch of each coil of the helix being approximately 45°. The inside diameter of the catheter tube 42 and its outside diameter is the same as described with reference to FIG. 1. Moreover the composition of the wires making up the flexible drive shaft 116 is also heat treated beryllium-copper.

It must be pointed out at this juncture that while the embodiment shown in FIG. 5 utilizes two helical wires to form the flexible drive shaft 116 such a construction is not required. Thus more than two wires can be used, providing that the wires are located so as to create a balanced load when driven by the motor.

It also must be pointed out at this juncture that in lieu of a single filament guide wire 114 a multi-filament wire or tube can be utilized. Moreover the guide wire itself can be formed as a spiral of filaments and/or tubes as shown in FIGS. 9 and 10, respectively.

The catheter 100 in FIG. 5 is arranged to be guided to its operative position within the artery by the use of the conventional guide wire 114. This action is accomplished by inserting the guide wire at the appropriate selected site in the body, such as into the femoral artery. The guide wire is then passed via the aorta into the coronary artery to the location of the restriction to be opened. The introduction of the guide wire can be aided by a fluoroscope, and a contrast medium can also be introduced into the artery. The recanalizing catheter 100 is then threaded down the guide wire 114 via the opening 112 and 104 at the distal end thereof and through the central passageway extending down the helical drive shaft 116 until the tip 24 of the catheter is located immediately adjacent the proximal end of the restriction to be opened. As in the other embodiment a suitable liquid is then introduced into the interior of the catheter tube 42 from a point adjacent the proximal end thereof to aid in lubricating and cooling the moving components within the catheter. Moreover the rotation of the helical coil drive shaft results in the creation of a pumping action on the introduced liquid. Thus, the liquid is aided in flowing down the catheter to the distal end. The liquid flows into communicating passages 62 from whence it flows out of the open interface 36. As described earlier this exiting liquid applies positive pressure to the vessel wall to move the vessel wall slightly outward radially so that damage to the wall by the cutter head 24 does not occur. In addition the flow of liquid outward through the interface 36 also precludes any fiberous tissue from snagging in the cutter head.

As will be appreciated by those skilled in the are in accordance with either embodiment of the invention the liquid which is passed down the catheter can, if desired, be oxygenated to eliminate distal ischemia during the restriction opening procedure by the catheter. Also, if desired, nitrates, contrast media or other drugs can be added to the liquid as needed during the procedure.

Without further elaboration, the foregoing will so fully illustrate my invention that others may, by applying current or future knowledge, readily adopt the same for use under various conditions of service.

I claim:

1. A catheter for introduction into a lumen in a living being to effect a procedure therein, said catheter being an elongated tubular flexible member having a distal end at which a working head is located, said catheter having an inner surface defining a passageway extending down said catheter, said working head being arranged for movement with respect to a central axis extending through said passageway, elongated drive means for said working head located within said passageway and extending down said catheter from a point adjacent said working head to a first remote proximal location, and an elongated bearing means for said drive means, said bearing means also located within said passageway and extending down said catheter from a point adjacent said working head to a second remote proximal location, one of said two last mentioned means being formed of at least a first wire and the other of said last two mentioned means being formed of a spiral of at least a second wire wrapped about said first wire, said second wire forming a helical space between its convolutions, whereupon said catheter can be readily bent through any arc up to a minimum radius of curvature while said drive means is rotated freely with respect to said bearing means and to said catheter at a high rotational speed to effect the movement of said working head with respect to said axis, said bearing means and said drive means cooperating with each other to maintain said drive means at a substantially neutral position within said catheter when said catheter is bent through said arc and rotated at said high rotational speed without resulting in undue vibration which could interfere with said procedure, said helical space being in communication with said inner surface and through which a cooling fluid may flow to contact said inner surface of said catheter and said first and second wires to expedite the rotation of said drive means with respect to said bearing means.

2. The catheter of claim 1 wherein said bearing means is formed as said spiral.

3. The catheter of claim 1 wherein said drive means is formed as said spiral

4. The catheter of claim 2 wherein said spiral bearing means includes a central passageway extending therethrough and wherein said drive means comprises a flexible shaft extending through said central passageway, said flexible shaft being arranged to rotate freely within said passageway.

5. The catheter of claim 4 wherein said spiral bearing means is centered within said catheter.

6. The catheter of claim 4 wherein said flexible drive means comprises at least one wire.

7. The catheter of claim 4 wherein said spiral bearing means is formed of a tough, yet flexible and relatively low frictional material.

8. The catheter of claim 7 wherein said material is beryllium-copper.

9. The catheter of claim 4 wherein said working head is rotary and said catheter includes bushing means adjacent its distal end and a working head mounting shaft to which said rotary working head is secured and wherein said flexible shaft is coupled to said working head mounting shaft adjacent the distal end of said flexible shaft.

10. The catheter of claim 3 wherein said spiral drive means includes a central passageway extending therethrough and wherein said bearing means comprises a flexible shaft extending through said central passageway, said spiral drive means being arranged to rotate freely about said flexible shaft when said shaft extends therethrough.

11. The catheter of claim 10 wherein said spiral drive means comprises at least one wire wound in a cylindrical helix.

12. The catheter of claim 11 wherein said bearing means comprises at least one wire.

13. The catheter of claim 10 wherein said spiral drive means is formed of a tough, yet flexible and relatively low frictional material.

14. The catheter of claim 13 wherein said material is beryllium-copper.

15. The catheter of claim 10 wherein said working head is rotary and said catheter includes bushing means adjacent its distal end and a working head mounting shaft to which said rotary working head is secured and wherein said flexible shaft is coupled to said working head mounting shaft adjacent the distal end of said flexible shaft.

16. The catheter of claim 11 wherein said spiral drive means comprises a pair of wires each wound as a cylindrical helix and interleaved with each other.

17. A flexible drive assembly comprising an elongated flexible tubular member including an inner surface defining a central passageway extending down its length and having a rear portion and a front portion, elongated drive means extending through said tubular member from a point adjacent said rear portion to a point adjacent said front portion, and elongated bearing means for said drive means, said bearing means extending within said tubular member from a point adjacent said front portion to a point adjacent said rear portion, one of said two last mentioned means being formed of at least a first wire and the other of said last two mentioned means being formed of a spiral of at least a second wire wrapped about said first wire, said second wire forming a helical space between its convolutions, whereupon said drive assembly can be readily bent through any arc up to a minimum radius of curvature while said drive means is rotated freely with respect to said bearing means at a high rotational speed, said bearing means and said drive means cooperating with each other so that said drive means is maintained at a neutral position within said tubular member as said tubular member is bent through said arc and rotated at said high rotational speed without undue vibration, said helical space being in communication with the inner surface of said tubular member and through which a cooling fluid may flow to contact said inner surface and said first and second wires to expedite the rotation of said drive means with respect to said bearing means.

18. The drive assembly of claim 17 wherein said bearing means is formed as said spiral.

19. The drive assembly of claim 17 wherein said drive means is formed as said spiral.

20. The drive assembly of claim 18 wherein said spiral bearing means includes a central passageway therethrough and wherein said drive means comprises a flexible shaft extending through said central passageway, said flexible shaft being arranged to rotate freely within said passageway.

21. The drive assembly of claim 20 wherein said spiral bearing means is centered within said tubular member.

22. The drive assembly of claim 20 wherein said drive means comprises at least one wire.

23. The drive assembly of claim 20 wherein said spiral bearing means is formed of a tough, yet flexible and relatively low frictional material.

24. The drive assembly of claim 23 wherein said material is beryllium-copper.

25. The drive assembly of claim 20 wherein said tubular member includes bushing means located adjacent its forward end and in which is located a mounting member for securement to a device to be rotated thereby, and wherein said flexible shaft is coupled to said mounting member adjacent the forward end of said flexible shaft.

26. The drive assembly of claim 19 wherein said spiral drive means includes a central passageway extending therethrough and wherein said bearing means comprises a flexible shaft extending through said central passageway, said spiral drive means being arranged to rotate freely about said flexible shaft.

27. The drive assembly of claim 19 wherein said spiral drive means comprises at least one wire wound in a cylindrical helix.

28. The drive assembly of claim 27 wherein said bearing means comprises at least one wire.

29. The drive assembly of claim 19 wherein said spiral drive means is formed of a tough, yet flexible and relatively low frictional material.

30. The drive assembly of claim 29 wherein said material is beryllium-copper.

31. The drive assembly of claim 19 wherein said tubular member includes bushing means located adjacent its forward end and which is arranged to be secured to a device to be rotated and wherein said flexible shaft is coupled to said bushing means adjacent the forward end of said flexible shaft.

32. The drive assembly of claim 27 wherein said spiral drive means comprises a pair of wires, each wound as a cylindrical helix and interleaved with each other.

* * * * *